United States Patent [19]
Chia et al.

[11] Patent Number: 5,868,741
[45] Date of Patent: Feb. 9, 1999

[54] ABLATION CATHETER SYSTEM HAVING FIXATION TINES

[75] Inventors: Weng-Kwen Raymond Chia, Irvine; Hosheng Tu, Tustin, both of Calif.

[73] Assignee: Irvine Biomedical, Inc., Irvine, Calif.

[21] Appl. No.: 93,479

[22] Filed: Jun. 8, 1998

Related U.S. Application Data

[62] Division of Ser. No. 861,271, May 21, 1997.

[51] Int. Cl.$^6$ ....................................................... A61B 17/39
[52] U.S. Cl. ............................................. 606/41; 607/128
[58] Field of Search ..................... 607/126–128, 607/130, 131; 600/375; 606/41, 45, 47, 49

[56] References Cited

U.S. PATENT DOCUMENTS

| 4,957,118 | 9/1990 | Eriebacher | 607/128 |
| 5,257,990 | 11/1993 | Nash | 606/45 |

*Primary Examiner*—William E. Kamm
*Assistant Examiner*—George R. Evanisko

[57] ABSTRACT

A catheter system having a tip with fixation tines for use in treatment of tissues, such as ablating tumors in a natural body conduit or a cavity by applying RF energy through the tip, wherein the catheter system passes through a natural body opening to reach the target tissues, wherein the catheter system stays at a desired position via its fixation tines and delivers therapeutic RF energy to the target tissues for improved tissue treatment.

4 Claims, 4 Drawing Sheets ns of the

ABLATION CATHETER SYSTEM HAVING FIXATION TINES

This is a division of Ser. No. 08/861,271, filed 1997 May 21.

FIELD OF THE INVENTION

The present invention generally relates to novel constructions for a catheter system. More particularly, this invention relates to a mapping and/or ablation catheter system with tine fixation means for use in mapping and/or treatment of cardiac tissues and in other medical applications, such as ablating tumors in a natural body conduit or a cavity by applying RF energy. The catheter system passes through a natural body opening to reach the target tissue, where the catheter stays in a desired position via its tine fixation means and maps the cardiac electrical potential as well as delivers therapeutic energy to the target tissues for improved treatment.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias, which are frequently caused by the presence of an "arrhythmogenic site" or "accessory atrioventricular pathway" close to the inner surface of the chambers of a heart. The heart includes a number of normal pathways, which are responsible for the propagation of electrical signals from the upper to lower chambers necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissues within the heart.

Of particular interest to the present invention are radiofrequency (RF) ablation protocols that have been proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissue in order to ablate the tissue of arrhythmogenic site or the accessory pathway. By successfully destroying that tissue, the abnormal signal patterns responsible for the tachycardia may be eliminated.

Typically a conventional electrophysiology catheter has had a tip that is very smooth and generally is hemispherically shaped and thus have a tendency to slip around in the chambers of the heart during the beating of the heart. This is particularly true in certain areas of the heart where it is difficult to apply positive pressure to the tip of the catheter. Because of the difficulty of retaining the tip of the catheter in certain position, the effectiveness of mapping and ablation is significantly compromised.

The "tip section" of a catheter is referred to here as the portion of that catheter containing at least one electrode. For illustration purposes, a catheter utilized in the endocardial radiofrequency ablation is inserted into a major vein or artery, usually in the neck or groin area. The catheter is then guided into an appropriate chamber of the heart by appropriate manipulation through a vein or artery.

The tip of a catheter must be maneuverable by a physician from the proximal end of the catheter, so that the electrodes at the tip section can be positioned against the tissue site to be ablated. The catheter must have a great deal of flexibility in order to follow the pathway of major blood vessels into the heart. It must permit user manipulation of the tip even when the catheter body is in a curved and/or twisted configuration. The tip section of a conventional electrophysiology catheter that is deflectable usually contains one large electrode about 4 mm in length for ablation purposes.

While a radiofrequency electrophysiology ablation procedure using an existing catheter has had promising results, the tip of a known catheter may not continuously contact the cardiac tissue intimately during the mapping and/or ablation period. Therefore there is a need for an improved catheter which can be utilized for mapping and ablation and in which is possible to temporarily affix the tip section of the catheter so that it will remain in a desired position on the wall of the heart during beating of the heart.

SUMMARY OF THE INVENTION

In general, it is an object of the present invention to provide an improved catheter which can be used in mapping and/or ablating cardiac tissues in the wall of a heart and which is provided with tine fixation means for retaining the tip section in a desired position on the wall of the heart. The capability of affixing the tip section of the catheter in place may also be applicable to means of ablating the tumors in a body natural conduit or a cavity.

In one embodiment, a catheter system comprises an inner catheter, having a flexible elongate tubular member having a distal section, and proximal and distal extremities, wherein the distal section has a thread for coupling purpose on the outside of the flexible elongate tubular member. An exchangeable handle is attached to the proximal extremity of the inner catheter. There is at least one ablation electrode mounted at the distal section of the flexible elongate tubular member of said inner catheter. Furthermore, a slidable catheter sheath is positioned outside of the inner catheter and has a distal section, a proximal end, a distal end, and a lumen extending therebetween, wherein a matching thread or tap hole for coupling purposes is disposed on the inner surface of the catheter sheath that is close to the distal end of the catheter sheath. The slidable catheter sheath further has a retractable tine fixation deployment means at the distal section of the catheter sheath, wherein said retractable tine fixation deployment means includes a plurality of spaced apart expandable members. The catheter system further comprises a non-deployed state for said retractable tine fixation deployment means when said catheter sheath is advanced into the body of a patient and/or is removed from the body, and further comprises a distended deployed state for said retractable tine fixation deployment means when said catheter system is positioned at the target location of the body.

Another object of the invention is to provide a catheter with retractable tine fixation deployment means in which the tine fixation means can be deployed and undeployed between the mapping and/or ablation operations. Another object of the invention is to provide a catheter with retractable tine fixation deployment means in which the tine fixation means can be readily maneuvered, applied, and controlled by a deployment mechanism at the handle.

The catheter system further comprises a steering mechanism at the handle for controlling the deflection of said distal section of the flexible elongate tubular member of the inner catheter. Usually a rotating ring or a push-pull plunger is employed in the steering mechanism. In another embodiment, the steerable ablation catheter comprises a bi-directional deflection or multiple curves deflection of the tip section having retractable tine fixation deployment means. One end of the steering wire is attached at certain point of the distal section of the flexible elongate tubular member of said inner catheter. The other end is attached to the steering mechanism at the handle. The steering mechanism on a steerable catheter or device is well known to those who are skilled in the art.

At least one conducting wire which is soldered to an electrode, passes through the lumen of the inner catheter and the interior void of the handle and is thereafter soldered to a contact pin of the connector which is secured at the proximal end of the handle. Therefrom, the conducting wire is connected to an external RF generator for ablation operations and/or to an EKG monitor for recording and display of the endocardial electrical signal.

In an additional embodiment, the catheter system further comprises a temperature sensing and close-loop temperature control mechanism for the catheter system having at least one temperature sensor on the distal section of the inner catheter. The location of the temperature sensor is preferably in the very proximity of one of the electrodes. In a still further embodiment, a method for operating an ablation catheter system of this invention further comprises a programmed temperature control mechanism for independently controlling the delivery of RF energy of each electrode of the ablation catheter.

In a still further embodiment, the distal section of the flexible elongate tubular member of the inner catheter comprises at least one ablation electrode which is formed of a conducting material, wherein the material for the electrode may consist of conductive metals such as platinum, iridium, gold, silver, stainless steel, Nitinol, or an alloy of their mixture. The conducting metal and its fabrication to form an electrode to be used in a catheter is well known to those who are skilled in the art.

The catheter system of this invention further comprises a plurality in excess of three spaced apart expandable members for the retractable tine fixation deployment means. In a preferred embodiment, the catheter system comprises a plurality in excess of five spaced apart expandable members for the retractable tine fixation deployment means. The construction material for the expandable members may be selected from the group of polyethylene, polyurethane, polyether block amide polymer, stainless steel, high strength Nitinol and the like. The expandable members are part of the catheter sheath that has a continuous linear smooth surface when the retractable tine fixation deployment means is at its undeployed state. The expandable members have a preshaped memory and extend to their preformed shape when the retractable tine fixation deployment means is deployed.

In another embodiment, the catheter system of this invention further comprises expandable members of said retractable tine fixation deployment means having a preshaped memory, and extending at an angle of less than 90 degrees, preferably less than 45 degrees, relative to the proximal side of the longitudinal axis of the inner catheter when the deployment means is deployed. In a further embodiment, the catheter system further comprises expandable members of said retractable tine fixation deployment means having a preshaped memory, and extending with a curved concave or convex fashion at an acute angle relative to the proximal side of the longitudinal axis of the inner catheter when the deployment means is deployed.

A method for operating a catheter system comprises: introducing the catheter system having an inner catheter and an outer catheter sheath under a non-deployed state into the body through a small surgery hole or through the natural body openings; and once approaching the target tissue, deploying the retractable tine fixation deployment means at the distal section of said catheter sheath by a deployment mechanism located at the handle. The method for operating a catheter system of this invention further comprises at least one ablation electrode mounted on the distal section of the flexible elongate tubular member of the inner catheter. The method for operating a catheter system further comprises measuring the endocardial electricity from or applying RF energy to the at least one electrode on the distal section of the flexible elongate tubular member of the inner catheter.

The catheter system of the present invention has several significant advantages over known catheter or ablation techniques. In particular, the catheter system having a retractable tine fixation deployment means may result in a firm and intimate tissue contact between the electrode and the target tissue during tissue ablation, resulting in a deep and large lesion which is highly desirable in tachycardia treatment.

BRIEF DESCRIPTION OF THE DRAWINGS

Additional objects and features of the present invention will become more apparent and the invention itself will be best understood from the following Detailed Description of the Preferred Embodiments, when read with reference to the accompanying drawings.

DETAILED DESCRIPTION OF THE PREFERRED EMBODIMENTS

Figure 1:
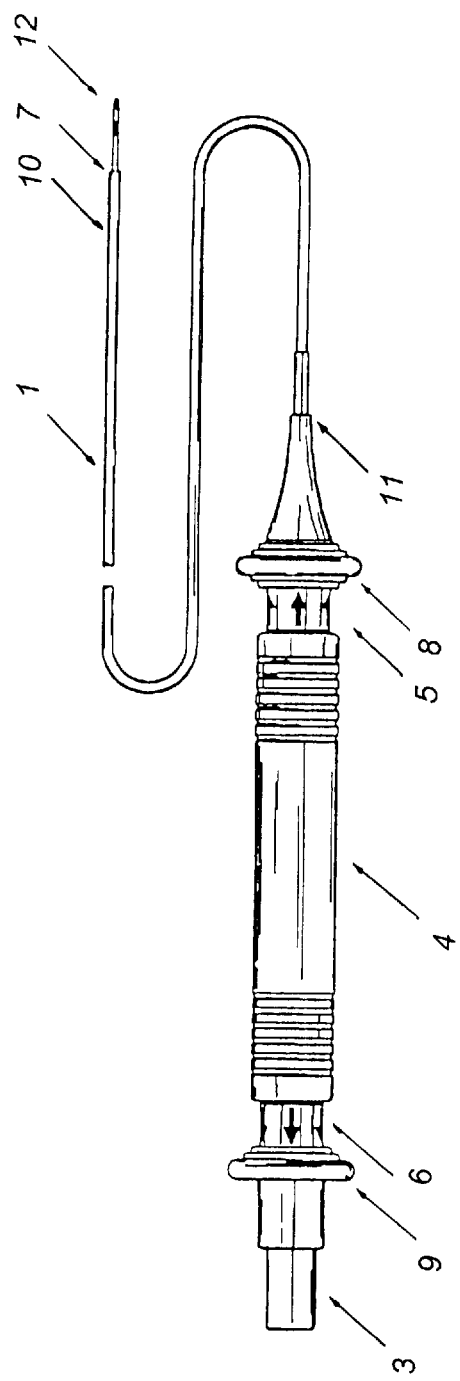
FIG. 1 is an overall view of the catheter system having a retractable tine fixation deployment means constructed in accordance with the principles of the present invention.

FIG. 1 shows an overall view of the catheter system having a distal section comprising retractable tine fixation deployment means. A catheter system constructed in accordance with the principles of the present invention comprises: a catheter sheath 1 having a distal tip section 10, a distal end 7, a proximal end 11, and at least one lumen extending therebetween. The catheter also comprises an inner catheter 12 that is longer than the catheter sheath 1 and is located within the lumen of the catheter sheath 1. A handle 4 is attached to the proximal end 11 of said catheter sheath 1 and/or the proximal end of the inner catheter.

A connector 3 secured at the proximal end of the catheter system, is part of the handle 4. The handle has one steering mechanism 5. The steering mechanism 5 is to deflect the tip section 13 of the inner catheter 12 for catheter maneuvering and positioning. By pushing the front plunger 8 of the handle 4, the tip section of the flexible elongate member of the inner catheter 12 deflects to one direction. By pulling back the front plunger 8, said tip section returns to its neutral position or to the other direction. In another embodiment, the steering mechanism 5 at the handle 4 comprises means for providing a plurality of deflectable curves on the distal tip section 13 of the inner catheter.

Figure 2:
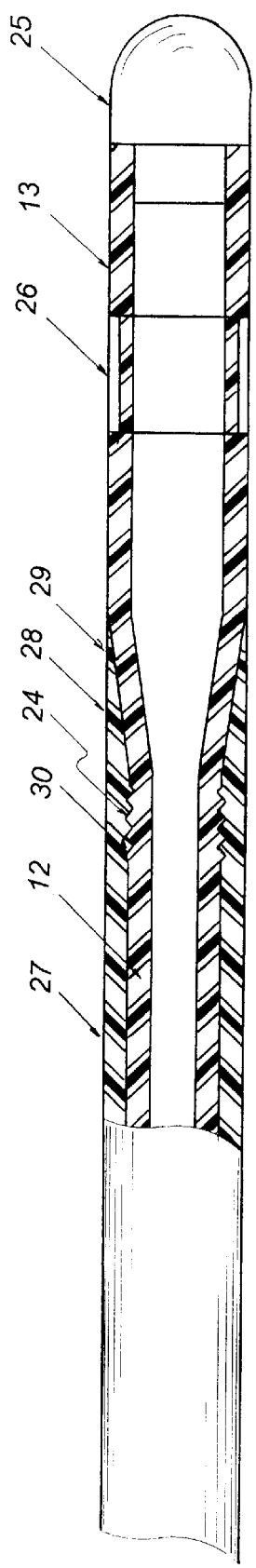
FIG. 2 is a close-up view of the distal section of the catheter system having a thread coupling means at non-deployed state.
Figure 3:
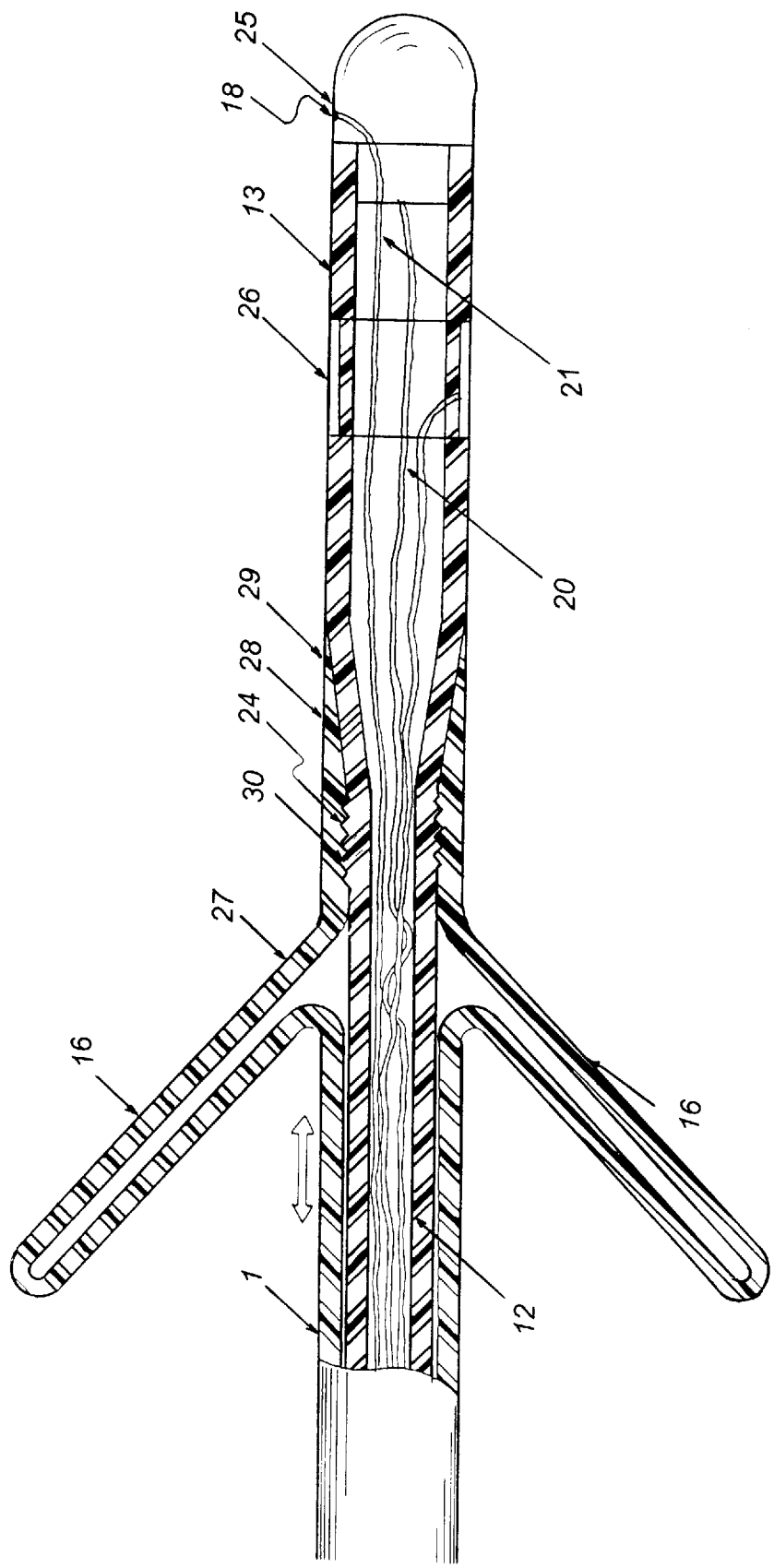
FIG. 3 is a close-up view of the distal section of the catheter system of FIG. 2 at fully deployed state.

FIG. 2 shows a close-up view of the distal section of the catheter system at non-deployed state. The catheter system comprises an inner catheter 12, having a flexible elongate tubular member having a distal section 13, and proximal and distal extremities, wherein the distal section has a thread 24 on the outside of the flexible elongate tubular member; an exchangeable handle attached to the proximal extremity of the inner catheter (not shown); at least one ablation electrode 25 or 26 is mounted on the distal section 13 of the flexible elongate tubular member of said inner catheter 12; and a slidable catheter sheath 27, having a distal section 28, a proximal end, a distal end 29, and a lumen extending therebetween, wherein a matching thread or tap hole 30 is disposed on the inner surface of and close to the distal end of the catheter sheath 27, and the catheter sheath further having a retractable tine fixation deployment means 16 at the distal section of the catheter sheath 27, wherein said retractable tine fixation deployment means includes a plurality of spaced apart expandable members 17. During operation, the inner catheter is inserted into the body of a patient, the inner catheter alone may function as an electrophysiology catheter for the purpose of mapping and/or ablation. When the catheter fixation need arises, the exchangeable handle is removed from the inner catheter, and a catheter sheath of this invention is inserted over the inner catheter. The catheter sheath and the inner catheter are engaged by coupling the matching thread of the catheter sheath and the thread of the inner catheter. After replacing the exchangeable handle, the catheter system is ready for operation having retractable tine fixation deployment means. After the operation is concluded, the coupled catheter system, including the catheter sheath and the inner catheter, is reversed to non-deployed state first and is thereafter removed from the body of a patient together as a catheter system.

Figure 4:
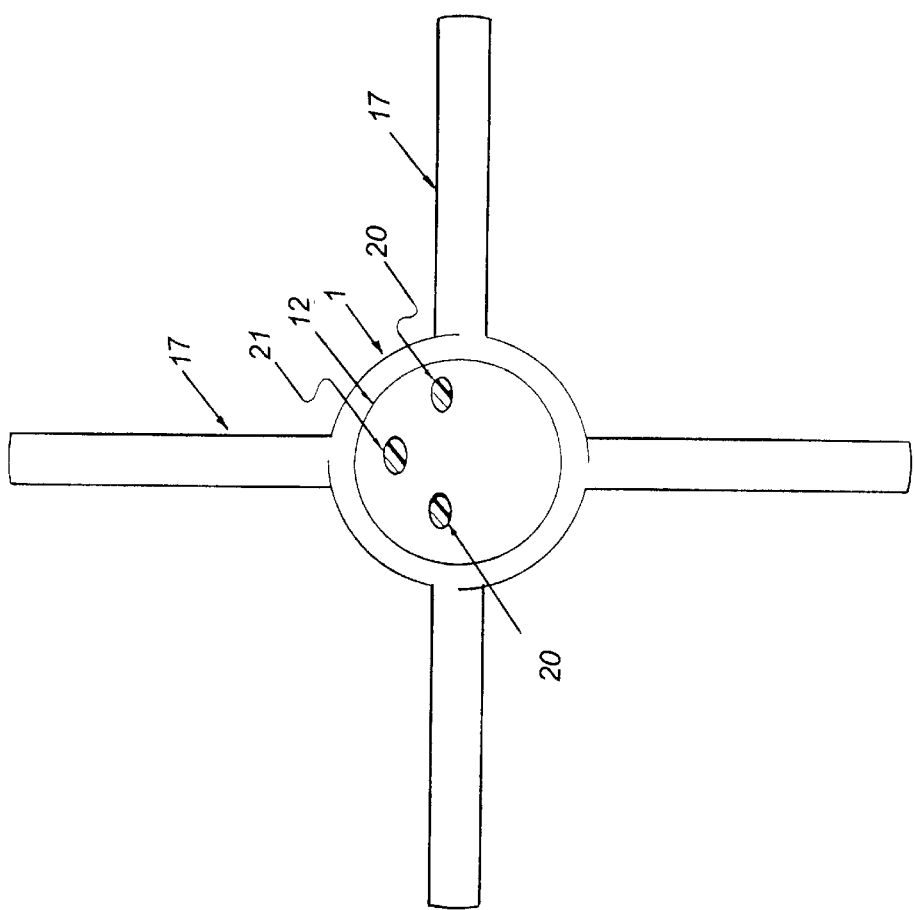
FIG. 4 is a cross-sectional view of the expandable members of the catheter sheath of FIG. 3.

The deployment of the retractable tine fixation deployment means 16 is controlled by a deployment mechanism 6 at the handle 4 (FIG. 1). A controlling ring 9 is used to deploy the retractable tine fixation deployment means 16 at the distal section 28 of the catheter sheath 27. FIG. 4 shows a cross-sectional view of the catheter system that comprises expandable members 17 of the retractable tine fixation deployment means 16, having a preshaped memory. The expandable members extend with a curved concave or convex fashion at an acute angle relative to the proximal side of the longitudinal axis of the inner catheter 12 when the deployment means 16 is deployed.

The electrode has an insulated conducting wire 20 secured to the ablation electrode, which passes through the lumen of the inner catheter 12 and is soldered to a contact pin of the connector 3 at the proximal end of the handle 4. The conducting wire from the connector end is externally connected to an EKG for diagnosis or to a RF generator during an electrophysiology ablation procedure. Therefrom, the RF energy is transmitted through the conducting wire to the electrode and delivered the energy to the target tissues.

A temperature sensor 18, either a thermocouple means or a thermister means, is constructed at the proximity of the electrodes 25 or 26 to measure the tissue contact temperature when RF energy is delivered. The temperature sensing wire 21 from the thermocouple or thermister is connected to one of the contact pins (not shown) of the connector 3 and externally connected to a transducer and to a close-loop temperature controller. The temperature reading is thereafter relayed to a close-loop controller to adjust the RF energy output to the electrode. The RF energy delivered is thus controlled by the temperature sensor reading or by a pre-programmed control algorithm.

From the foregoing, it should now be appreciated that an improved ablation catheter having retractable tine fixation deployment means has been disclosed for mapping and/or ablation procedures, including endocardial, epicardial, or body tissues. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:

(a) an inner catheter comprising a flexible elongate tubular member, the tubular member having a distal section, a proximal extremity, and a distal extremity, wherein the distal section has a thread on an outside surface of the flexible elongate tubular member;

(b) a handle attached to the proximal extremity of the flexible elongate tubular member;

(c) at least one ablation electrode mounted on the distal section of the flexible elongate tubular member of the inner catheter; and (d) a slidable catheter sheath having a sheath distal section, a proximal end, a distal end, and a lumen extending between the proximal end and the distal end, wherein a matching thread is disposed on an inner surface of the catheter sheath that is close to the distal end of the catheter sheath, the slidable catheter sheath further having means for retractable tine fixation deployment at the sheath distal section, wherein the means for retractable tine fixation deployment includes a plurality of spaced apart expandable members, wherein the retractable tine fixation means has a non-deployed state and a distended deployed state, whereby the non-deployed state is used for advancing and removing the catheter and the distended deployed state is used for fixing the catheter to a targeted location, wherein the slidable catheter sheath is disposed over the inner catheter sheath past the distal section thread and the catheter sheath matching thread is connected to the distal section thread.

2. The catheter system of claim 1, wherein the expandable members of said means for retractable tine fixation deployment have a preshaped memory, and extend with a curved fashion at an acute angle relative to the catheter sheath when the deployment means is deployed.

3. The catheter system as in claim 1 further comprising a steering mechanism at the handle for controlling a deflection of the distal section of the flexible elongate tubular member of said inner catheter.

4. The catheter system of claim 1, wherein the handle has means for exchangeably coupling the handle to the inner catheter.

* * * * *